United States Patent
Farrell

(10) Patent No.: US 6,350,740 B1
(45) Date of Patent: *Feb. 26, 2002

(54) TRANSPLATINUM COMPLEXES AS CYTOTOXIC AND ANTICANCER AGENTS

(75) Inventor: Nicholas Farrell, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/654,882

(22) Filed: Sep. 5, 2000

(51) Int. Cl.$^7$ ............................ A61K 33/24; C07F 15/00
(52) U.S. Cl. ................... 514/185; 514/184; 514/186; 514/187; 514/188; 514/492; 544/225; 546/2; 546/10; 556/137; 548/101; 548/108
(58) Field of Search ................... 514/185, 186, 514/187, 188, 492, 184; 544/225; 546/2, 10; 556/137; 548/101, 108

(56) References Cited

U.S. PATENT DOCUMENTS 5,624,919 A * 4/1997 Farrell ..................... 514/184
6,113,934 A * 9/2000 Farrell et al. ............. 424/405

OTHER PUBLICATIONS

Balasubramanian et al Ann. Rep. Med. Chem. 33 (1998) 151–162.*

Bierbach et al Inorg. Chem. 36 (1997) 3657–3665.*

Draetta et al Ann. Rep. Med. Chem. 31 (1996) 241–248.*

Hofr et al J. Biol. Chem. 276 (2001) 9655–9661.*

Ivanov et al Chemical Abstract 123:275180, 1995.*

Sundquist et al Inorg. Chem. 26 (1987) 1524–1528.*

* cited by examiner

Primary Examiner—Richard L. Raymond
(74) Attorney, Agent, or Firm—Whitham, Curtis & Christofferson, PC

(57) ABSTRACT

The invention provides a method for enhancing the water solubility of cytotoxic trans-platinum complexes. The present invention also provides a method for killing tumor cells, and a method for the treatment of tumors by the administration of a cytotoxic platinum coordination complex of the general formula SP4-2-[PtX(L)(L')(B)]$^+$.

38 Claims, No Drawings

TRANSPLATINUM COMPLEXES AS CYTOTOXIC AND ANTICANCER AGENTS

CROSS REFERENCE TO RELATED APPLICATIONS

This application is related to U.S. Pat. No. 6,113,934 the contents of which is herein incorporated by reference.

This invention was made using funds from grants from the National Science Foundation having grant number 5-23175. The government may have certain rights in this invention.

DESCRIPTION

BACKGROUND OF THE INVENTION

FIELF OF THE INVENTION

The invention generally relates to a method for water-solubilization of cytotoxic trans-platinum compounds and to a method of killing tumor cells. In particular, the invention provides cytotoxic platinum compounds of the general formula SP-4-2-[PtX(L)(L')(B)]+for the treatment of tumors.

BACKGROUND OF THE INVENTION

The use of cisplatin, cis-[PtCl$_2$(NH$_3$)$_2$], and carboplatin, [Pt(CBDCA)(NH$_3$)$_2$] (CBDCA=1,1-cyclobutanedicarboxylate), in the treatment of certain cancers is well-established. Nevertheless, there is a continued interest in the design of structurally novel platinum compounds that show antitumor activity complementary to that of the clinical drugs. The fact that transplatin, trans-[PtCl$_2$(NH$_3$)$_2$],

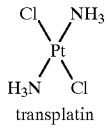

transplatin was found to be therapeutically inactive, has been considered a paradigm for the structure-activity relationships (SAR) of platinum(II) antitumor compounds; trans-Pt compounds have been dismissed as ineffective in vivo agents.

However, the presence of a planar ligand such as pyridine or quinoline, e.g., in trans-[PtCl$_2$ (NH$_3$) (quinoline)],

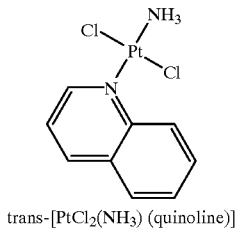

trans-[PtCl$_2$(NH$_3$) (quinoline)]

dramatically enhances the in vitro cytotoxicity of the trans geometry [Farrell, N., Kelland, L. R., Roberts, J. D. and Van Beusichem, M.: Activation of the Trans Geometry in Platinum Antitumor Complexes. A Survey of the Cytotoxicity of Trans Complexes Containing Planar Ligands in Murine L1210 and Human Tumor Panels and Studies on Their Mechanism of Action. Cancer Res. 52:5065 (1992); Van Beusichem, M. and Farrell, N.: Activation of the Trans Geometry in Platinum Antitumor Complexes. Synthesis, Characterisation and Biological Activity of Complexes with Planar Ligands Pyridine, N-Methylimidazole, Thiazole and Quinoline. The Crystal and Molecular Structure of trans-dichlorobis(thiazole)platinum(II). Inorg. Chem. 31:634 (1992)] The cytotoxic activity of such "nonclassical" trans-platinum complexes has been discussed in terms of both an overall altered affinity toward biologically relevant (N and S) nucleophiles and unique DNA binding modes. Importantly, the newer trans-platinum compounds containing planar ligands display a different profile of cytotoxicity in comparison to cisplatin and retain their cytotoxic activity in cisplatin-resistant tumor cells. Thus, there is reason to believe that a trans-platinum compound in the clinic would have activity complementary to cisplatin, resulting in significant benefits to patients. However, such "nonclassical" trans-platinum species have been found to have limited bioavailability and, consequently, low in vivo activity. One possible explanation is lack of water solubility.

It would be highly desirable to have available additional platinum species for the treatment of cancer. It would be especially desirable if such compounds displayed high levels of cytotoxicity and were also water-soluble, thereby enhancing their bioavailability and potential in vivo usefulness for the treatment of tumors.

SUMMARY OF THE INVENTION

It is an object of this invention to provide a method for enhancing water-solubility and cytotoxicity of the trans-platinum geometry through production of cationic compounds.

It is a further object of this invention to provide a method for killing tumor cells and treating tumors in patients, comprising the step of administering to a patient in need thereof an effective amount of a platinum coordination compound of the general formula SP-4-2-[PtX(L)(L')(B)]$^+$ where X is an anionic ligand; L and L' represent ammines (NH$_3$) or substituted or unsubstituted heterocyclic amines where the substituents are electrophilic or nucleophilic, and L and L' may be the same or different, and B is a sulfoxide, usually dimethylsulfoxide R$^2$R$^3$SO (where R$^2$=methyl and R$^3$=methyl; however it should be understood that other alkyl substituted sulfoxides may be used in this invention and that R$^2$ and R$^3$ may be the same or different) or a heterocyclic nucleobase with a nitrogen in a ring which is connected to Pt.

In preferred embodiments of the present invention, the platinum coordination compound is trans-[PtCl(Me$_2$SO)(pyridine)$_2$]$^+$, or trans-[PtCl(9-ethylguanine)(NH$_3$)$_2$]$^+$, or SP-4-2-[PtCl(9-ethylguanine)(NH$_3$)(thiazole)]$^+$, or SP-4-2-[PtCl(9-ethylguanine) (NH$_3$)(benzothiazole)]$^+$, or SP-4-2-[PtCl 9-ethylguanine)(NH$_3$)(quinoline)]$^+$, or SP-4-2-[PtCl (9-ethylguanine)(NH$_3$)(isoquinoline)]$^+$, or trans-[PtCl(9-ethylguanine) (4-picoline)$_2$]$^+$, or trans- [PtCl(1-methylcytosine)(NH$_3$)$_2$]$^+$, or SP-4-2-[PtCl (1-methylcytosine)(NH$_3$)(thiazole)],$^+$ or SP-4-2-[PtCl(1-methylcytosine)(NH$_3$)(quinoline)]$^+$, or SP-4-2-[PtCl(1-methylcytosine)(NH$_3$)(isoquinoline)]$^+$. Administration may be oral or parenteral.

It is a further object of the instant invention to provide new compositions of matter in the form of platinum coordination compounds: trans-[PtCl(Me$_2$SO)(pyridine)$_2$]$^+$, SP-4-2-[PtCl(9-ethylguanine)(NH$_3$)(thiazole)]$^+$, SP-4-2-[PtCl(9-ethylguanine)(NH$_3$) (benzothiazole)]$^+$, SP-4-2-[PtCl(9-ethylguanine)(NH$_3$)(isoquinoline)]$^+$, trans-[PtCl (9-ethylguanine)(4-picoline)$_2$]$^+$, trans-[PtCl(1-methylcytosine)(NH$_3$)$_2$]$^+$, SP-4-2-[PtCl(1-methylcytosine)

$(NH_3)(thiazole)]^+$, SP-4-2-[PtCl (1-methylcytosine)(quinoline)]$^+$, and SP-4-2-[PtCl(1-methylcytosine)(NH$_3$)(isoquinoline)]$^+$.

DETAILED DESCRIPTION OF THE PREFERRED EMBODIMENTS OF THE INVENTION

Platinum compounds of the general formula [PtXA$_m$B$_{3-m}$], which show excellent solubility, have been previously described as anti-viral agents (U.S. Pat. No. 6,113,934, the complete contents of which is herein incorporated by reference). Surprisingly, some of these compounds also display cytotoxic properties. Therefore, the present invention provides novel forms of such compounds, a method for water-solubilization of cytotoxic trans-platinum compounds, a method for the use of such compounds as cytotoxic agents, and a method of use of such compounds to treat tumors. These compounds are prepared as salts, the cationic component of which is described by the formula SP-4-2[PtX(L)(L')(B)]$^+$.

It is an object of the present invention to provide a method of killing tumor cells and treating tumors by the administration of platinum complexes of the general formula:

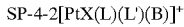
SP-4-2[PtX(L)(L')(B)]$^+$

In this formula:
- a) X represents an anionic ligand such as halogens (e.g., Cl, Br, or I), alkoxides (e.g., OR where R=CH$_3$, C$_2$H$_5$, or other lower alkyls), sulfhydryls (SR where R=CH$_3$, C$_2$H$_5$, or other lower alkyls, where C$_{1-12}$ is preferred), and carboxylates (RCOO$^-$ where R=CH$_3$, C$_2$H$_5$, etc.) .Chloride is the preferred anionic ligand;
- b) L and L' represent ammines (NH$_3$ linked directly to the platinum metal), or substituted or unsubstituted heterocyclic amines, where the substituents are electrophilic or nucleophilic (e.g. C$_{1-12}$ alkyl, —NO$_2$, —X (Cl, Br, I), -NR$_2$ where R is C$_{1-12}$ alkyl, -COOR where R is C$_{1-12}$ alkyl). Preferred heterocycles include but are not limited to thiazole, benzothiazole, imidazole, quinoline, isoquinoline, and picoline. Other useful heterocycles may include oxazole, indole, and acridine. L and L' may be the same of different. Further, L and L' are located "trans" to one another in the compounds. Note that, because four different substituents are present, "cis-trans" designations technically do not apply. The nomenclature "SP-4-2" follows the rules from Nomenclature of Inorganic Chemistry, Recommendations 1990, Blackwell Publicaitons, 1990. Edited by G. J. Leigh. [ISBN 0-632-02319-8; 0-6323-02494-1]. This nomenclature indicates that the compounds are square planar Pt II compounds in which the two centrally named substituents, L and L', are located trans to each other as depicted below:

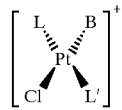

- c) B represents either of (i) or (ii):
  - i) a sulfoxide, R$^2$R$^3$ SO where R$^2$and R$^3$ may be the same or different and represent alkyl or aryl substituents. In a preferred embodiment of the present invention, the sulfoxide is dimethylsulfoxide (where R$^2$=methyl and R$^3$=methyl). In yet another embodiment, R$^2$=methyl and R$^3$=benzyl;
  - ii) a nitrogen-containing nucleobase where the nitrogen is connected to the Pt moiety. Examples of such nucleobases include but are not limited to: purines and purine compounds (e.g. guanine, 9-ethylguanosine, adenine, hypoxanthine, xanthine, uric acid, caffeine, threobromine, and the like); pyrimidines and pyrimidine compounds (e.g. uracil, thymine, cytosine, methylcytosine, and the like); nucleosides (e.g. guanosine and the like); nucleotides (e.g. 5'-guanosinemonophosphate and the like); and oligonucleotides or defined polynucleotide sequences [e.g. deoxyribonucleic acid (DNA), ribonucleic acid (RNA), or peptidonucleice acids (PNA)]. The preferred binding site of endocyclic nitrogens is N7 for purines and N3 for pyrimidines. Other ligands similar to nucleobases may also be used, for example, hydantoin.

The compounds in the present invention are usually cations and are prepared as salts. In depictions of the formulas in the text of the application, the counterion is omitted for simplicity. In preferred embodiments of the instant invention, the platinum compounds are prepared as nitrate salts. Other common counter-anions which may be utilized in the practice of the present invention include but are not limited to Cl$^-$, ClO$_4^-$, PF$_6^-$, and BF$_4^-$.

Chemical Syntheses

Nucleobase Compounds

SP-4-2-[PtCl(nucleobase)(L)(L')]NO$_3$. These compounds were prepared according to the published method (Bierbach U, Farrell N (1998) JBIC 3: 570-580).

To a solution of:
- i) 1 mmol of trans-[PtCl$_2$(L)(L')] (wherein L=L'=NH$_3$, or L=L'=pyridine), or
- ii) trans-[PtCl$_2$(NH$_3$)(L)] where L=pyridine or a planar amine as above; in 25 ml of anhydrous dimethylformamide (DMF) was added 0.170 g (1 mmol) of AgNO$_3$. After stirring this mixture at room temperature in the dark for 48 hours, the precipitated AgCl was filtered off through a Celite pad. To the filtrate was added (1 mmol) of 9-ethylguanine (or other suitable nucleobase) and the mixture was allowed to stir for 48 hours. The DMF was removed under reduced pressure at 30° C. After addition of 50 mL of diethyl ether, the remaining oil solidified. The obtained crude products was recrystallized from methanol or cold water. Identity of products was confirmed by NMR spectroscopy and elemental analysis.

Sulfoxides

SP-4-2-[PtCl(R$^2$R$^3$ SO)(L)(L')]NO$_3$. These compounds contain a sulfoxide as ligand B. They were prepared in basically the same manner with slight modifications in work-up and crystallisation. The preparation is exemplified for the Me$_2$SO case.

trans-[PtCl(Me$_2$SO)(py)$_2$]NO$_3$ To a suspension of trans-[PtCl$_2$(py)$_2$] (1.0 g, 2.4 mmol) in 30 mL of MeOH was added AgNO$_3$ (0.4 g, 2.4 mmol) and Me$_2$SO (2 mL, 2.2 g, 28 mmol). The reaction mixture was stirred at 80° C. overnight. The insoluble AgCl precipitate was filtered off and the filtrate was evaporated down. To the oil was added 2 ml of MeOH when a white solid precipitated out after stirring for about 10 minutes. Ether was then added to intensify the precipitation. After cooling overnight, the white solid was filtered off and recrystallized from hot MeOH/ ether. The product was dried in vacuum with heat. Yield 66 %. Anal. Calcd. for $C_{12}H_{16}ClN_3O_4SPt$: C, 27.25; H, 3.03; N, 7.95. Found C, 26.71; H, 2.95; N 7.56.

trans-[PtCl (MeBzSO)(Py)$_2$]NO$_3$ The same general conditions were used as for the previous complex but with two equivalents of sulfoxide ligand. Upon evaporation to an oil, acetone was added to dissolve the excess of MeBzSO and the product was precipitated out with ether. Upon cooling, the white solid was filtered off, recrystallized from MeOH/ether and washed with acetone to remove any remaining free ligand. The product was dried in vacuum with heat. Yield 45 % Anal. Calcd. for $C_{18}H_{20}ClN_3O_4SPt$: C, 35.73; H, 3.31; N, 6.95. Found C, 35.93; H, 3.11; N, 6.70.

trans-[PtCl(Me$_2$SO)(pic)$_2$]NO$_3$. The same general reaction conditions were used as above. Yield 68 % Anal. Calcd. for $C_{14}H_{20}ClN_3O_4SPt$: C, 30.19; H, 3.59; N, 7.55. Found C, 30.51; H, 3.94; N, 7.53.

trans-[PtCl (MeBzSO)(pic)$_2$]NO$_3$. The same general conditions were used as above but again with two equivalents of sulfoxide ligand. Upon evaporation to an oil the product was precipitated out with ether. After cooling overnight, the white solid was filtered off, recrystallized from hot MeOH/ether and washed with acetone to remove the excess of free ligand. The product was dried in vacuum with heat. Yield 53 % Anal. Calcd. for $C19H_{22}ClN_3O_4SPt$: C, 37.94; H, 3.79; N, 6.64. Found C, 38.08; H, 3.73; N, 6.63.

Implementation of the claimed invention will generally involve identifying patients suffering from tumors and administering the platinum coordination compound in an acceptable form by an appropriate route. The dosage to be administered is usually determined in Phase I clinical trials and may vary depending on the age, gender, weight and overall health status of the individual patient, as well as the nature of the cancer itself.

Administration can be oral or parenteral, including intravenously, intramuscularly, subcutaneously, etc., or by other routes (e.g. transdermal, sublingual, aerosol, etc.).

The compounds can be administered in the pure form or in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of 1–99% of the composition and the vehicular "carrier" will constitute 1–99% of the composition. The pharmaceutical compositions of the present invention may include any suitable pharmaceutically acceptable additives or adjuncts to the extent that they do not hinder or interfere with the therapeutic effect desired of the Pt complex.

The administration of pharmaceutical compositions of the present invention can be intermittent, or at a gradual or continuous, constant or controlled rate to a patient. In addition, the time of day and the number of times per day that the pharmaceutical formulation is administered can vary. Further, the effective dose can vary depending upon factors such as the mode of delivery, gender, age, and other conditions of the patient, as well as tumor type and stage or grade.

Generally, for parenteral administration in humans, dosages in the range of from about 0.1 to about 500 mg active Pt compound/kg body weight/24 hr., more preferably 1.0 to 10.0 active Pt compound/kg body weight/24 hr., are effective. The level of efficacy and optimal amount of dosage for any given Pt complex may vary from complex to complex.

In the following examples, objects and advantages of this invention are further illustrated by various embodiments thereof but the details of those examples should not be construed to unduly limit this invention.

EXAMPLES

Methods

The cytotoxicity of the novel trans-platinum compounds was assayed through the standard protocols of the NCI Developmental Therapeutics (HIV) and NIAID (Herpes Viruses) Screening Programs.

See the following websites for details of the protocols:
http://dtp.nih.gov/docs/aids/aids screen.html
http://www.niaid.nih.gov/dmid/apdsame.html. $IC_{50}$ is cytotoxic dose in cell carriers.

EXAMPLE 1

Cytotoxicity Studies with Platinum Nucleobase Compounds

The cytotoxicity of several nucleobase compounds of the general formula SP-4-2-[PtX(L)(L')(B)]$^+$ was assessed and the results are given in Table I. The cell lines employed were human foreskin fibroblast (HFF), Daudi, and CEM-SS, a T-cell line typically used to csrry snd maintain human imnmunodefficiency virus (HIV). The $lC_{50}$ values for HFF and Dsudi cell lines were determined by cell proliferation as referenced above. The $IC_{50}$ values for the CEM-SS cell line was determined by XTT colorimetric assays as referenced above.

The following abbreviations apply to Table II: 4-pic, 4-picoline; tz, thiazole; bztz, benzothiazole; quin, quinoline; iquin, isoquinoline; 9-EtGua, 9-ethylguanine; 1-MeCyt, 1-methylcytosine.

TABLE I

| | | | | $IC_{50}$ ($\mu$M) for indicated cell line | | | |
|---|---|---|---|---|---|---|---|
| Compound | L | L' | B | HFF | Daudi | CEM-SS | CEM-SS |
| 1 | NH$_3$ | NH$_3$ | 9-EtGua | 18.9 | 7.9 | | |
| 2 | NH$_3$ | tz | 9-EtGua | 11.2 | 18.1 | 47.3 | 24.6 |
| 3 | NH$_3$ | bztz | 9-EtGua | 11.2 | 9.8 | | |
| 4 | NH$_3$ | quin | 9-EtGua | 25.9 | 0.93 | 47.4 | 31.7 |
| 5 | NH$_3$ | iquin | 9-EtGua | 2.8 | 4.8 | | |
| 6 | 4-pic | 4-pic | 9-EtGua | 21.7 | 0.92 | 1.9 | 2.0 |
| 7 | NH$_3$ | NH$_3$ | 1-MeCyt | >45.2 | 15.0 | | |
| 8 | NH$_3$ | tz | 1-MeCyt | >52.0 | | | |
| 9 | NH$_3$ | quin | 1-MeCyt | 38.7 | 14.1 | 50.4 | 33.2 |
| 10 | NH$_3$ | iquin | 1-MeCyt | >56.4 | 21.6 | | |

As can be seen, some exceptionally cytotoxic agents such as Compound 6 were produced. The cytotoxicity is equivalent to that of parent trans-[PtCl$_2$(4-pic)$_2$] but Compound 6 adds significant water-solubility and bioavailability over the parent compound. Such toxic activity has previously correlated well with that of water-soluble platinum compounds such as cisplatin. Therefore, it is likely that these and other similar compounds of the general formula $[PtX(L)(L')(B)]^+$ will display anti-tumor activity in vivo.

EXAMPLE 2

Cytotoxicity Studies with Platinum Sulfoxide Compounds

The cytotoxic properties of the platinum complex trans-$[PtCl(Me_2SO)(pyridine)_2]^+$ were assessed both in vitro and in vivo. The results, which are depicted below in Table II, showed in vitro cytotoxicity equivalent to the parent trans-$[PtCl_2(pyridine)_2]$ in human ovsrian A780 cells. In initial in vivo studies in animals (murine L1210 leukemia), the dimethysulfoxide complex exhibited some antitumor activity (T/C of>150% is considered indicative of in vivo activity). In contrast, as previously found and reported (J. Med. Chem. 32:2240 (989) the parent dichloride is totally inactive. Thus, the concept of water-solubilization to give equivalent cytoxicity and enhanced in vivo activity is confirmed.

TABLE II

| | Complex | |
|---|---|---|
| | A 2780[a] $IC_{50}(\mu g/mL)$ | L1210 Leukemia[b] % T/C (Dose, schedule) |
| trans-$[PtCl(Me_2SO)(pyridine)_2]^+$ | 0.3 | 155 (50 × 3) |
| trans-$[PtCl_2(pyridine)_2]$ | 0.2 | 106 (50 × 2) | a: $IC_{50}$ values calculated according to Farrell, N., Tam, T. B. Ha, Souchard, J.-P., Wimmer, F. L., Cros, S., and Johnson, N. P.: Cytostatic trans-Platinum(II) Complexes. J. Med. Chem. 32:2240 (1989) and Farrell, N., Qu, Y., and Hacker, M. P.: Cytotoxicity and Antitumor Activity of Bis(platinum) Complexes. A Novel Class of Platinum Complexes Active in Cell Lines Resistant to Both Cisplatin and 1,2-Diaminocyclohexane Complexes. J. Med. Chem. 33:2179 (1990).

b: %T/C is % average survival in days of treated animals/average survival in days of control animals. All tests performed as reported in references in a above. 50×3 refers to dose (mg/kg) and schedule (drug injection at 1,5,9 days after tumor inoculation). The parent dichloride was injected twice only because treated animals died at same rate of controls, again indicating no activity.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for treating tumors in patients, comprising the step of administering to a patient in need thereof an effective amount of a platinum coordination compound wherein said platinum coordination compound is a salt, the cationic component of which is:

$$SP\text{-}4\text{-}2\text{-}[PtX(L)(L')(B)]^+$$

wherein,

X is an anionic ligand;

L and L' are selected from the group consisting of $NH_3$ and heterocyclic amines where the substituents are electrophilic or nucleophilic, and L and L' may be the same or different, and B is a sulfoxide or a nitrogen-containing nucleobase with a nitrogen in a ring which is connected to Pt.

2. The method of claim 1 wherein said cationic component of said platinum coordination compound is trans-$[PtCl(Me_2SO)(pyridine)_2]^+$.

3. The method of claim 1 wherein said cationic component of said platinum coordination compound is trans-$[PtCl(9\text{-}ethylguanine)(NH_3)_2]^+$.

4. The method of claim 1 wherein said cationic component of said platinum coordination compound is SP-4-2-$[PtCl(9\text{-}ethylguanine)(NH_3)(thiazole)]^+$.

5. The method of claim 1 wherein said cationic component of said platinum coordination compound is SP-4-2-$[PtCl(9\text{-}ethylguanine)(NH_3)(benzothiazole)]^+$.

6. The method of claim 1 wherein said cationic component of said platinum coordination compound is SP-4-2-$[PtCl(9\text{-}ethylguanine)(NH_3)(quinoline)]^+$.

7. The method of claim 1 wherein said cationic component of said platinum coordination compound is SP-4-2-$[PtCl(9\text{-}ethylguanine)(NH_3)(isoquinoline)]^+$.

8. The method of claim 1 wherein said cationic component of said platinum coordination compound is trans-$[PtCl(9\text{-}ethylguanine)(4\text{-}picoline)_2]^+$.

9. The method of claim 1 wherein said cationic component of said platinum coordination compound is trans-$[PtCl(1\text{-}methylcytosine)(NH_3)_2]^+$.

10. The method of claim 1 wherein said cationic component of said platinum coordination compound is SP-4-2-$[PtCl(1\text{-}methylcytosine)(NH_3)(thiazole)]^+$.

11. The method of claim 1 wherein said cationic component of said platinum coordination compound is SP-4-2-$[PtCl(1\text{-}methylcytosine)(NH_3)(quinoline)]^+$.

12. The method of claim 1 wherein said cationic component of said platinum coordination compound is SP-4-2-$[PtCl(1\text{-}methylcytosine)(NH_3)(isoquinoline)]^+$.

13. The method of claim 1 wherein said step of administration is oral or parenteral.

14. A method of killing tumor cells, comprising the step of contacting said tumor cells with a platinum coordination compound wherein said platinum coordination compound is a salt, the cationic component of which is:

$$SP\text{-}4\text{-}2\text{-}[PtX(L)(L')(B)]^+$$

wherein,

X is an anionic ligand;

L and L' are selected from the group consisting of $NH_3$ and heterocyclic amines where the substituents are electrophilic or nucleophilic, and L and L' may be the same or different, and B is a sulfoxide or a nitrogen-containing nucleobase with a nitrogen in a ring which is connected to Pt.

15. The method of claim 14 wherein said cationic component of said platinum coordination compound is trans-$[PtCl(Me_2SO)(pyridine)_2]^+$.

16. The method of claim 14 wherein said cationic component of said platinum coordination compound is trans-$[PtCl(9\text{-}ethylguanine)(NH_3)_2]^+$.

17. The method of claim 14 wherein said cationic component of said platinum coordination compound is SP-4-2-$[PtCl(9\text{-}ethylguanine)(NH_3)(thiazole)]^+$.

18. The method of claim 14 wherein said cationic component of said platinum coordination compound is SP-4-2-[PtCl(9-ethylguanine)(NH$_3$)(benzothiazole)]$^+$.

19. The method of claim 14 wherein said cationic component of said platinum coordination compound is SP-4-2-[PtCl(9-ethylguanine)(NH$_3$)(quinoline)]$^+$.

20. The method of claim 14 wherein said cationic component of said platinum coordination compound is SP-4-2-[PtCl(9-ethylguanine)(NH$_3$)(isoquinoline)]$^+$.

21. The method of claim 14 wherein said cationic component of said platinum coordination compound is trans-[PtCl(9-ethylguanine)(4-picoline)$_2$]$^+$.

22. The method of claim 14 wherein said cationic component of said platinum coordination compound is trans-[PtCl(1-methylcytosine)(NH$_3$)$_2$]$^+$.

23. The method of claim 14 wherein said cationic component of said platinum coordination compound is SP-4-2-[PtCl(1-methylcytosine)(NH$_3$)(thiazole)]$^+$.

24. The method of claim 14 wherein said cationic component of said platinum coordination compound is SP-4-2-[PtCl(1-methylcytosine)(NH$_3$)(quinoline)]$^+$.

25. The method of claim 14 wherein said cationic component of said platinum coordination compound is SP-4-2-[PtCl(1-methylcytosine)(NH$_3$)(isoquinoline)]$^+$.

26. The method of claim 14 wherein said step of administration is oral or parenteral.

27. A platinum coordination compound wherein said platinum coordination compound is a salt, the cationic component of which is trans-[PtCl(Me$_2$SO)(pyridine)$_2$]$^+$.

28. A platinum coordination compound wherein said platinum coordination compound is a salt, the cationic component of which is SP-4-2-[PtCl(9-ethylguanine)(NH$_3$)(thiazole)]$^+$.

29. A platinum coordination compound wherein said platinum coordination compound is a salt, the cationic component of which is SP-4-2-[PtCl(9-ethylguanine)(NH$_3$)(benzothiazole)]$^+$.

30. A platinum coordination compound wherein said platinum coordination compound is a salt, the cationic component of which is SP-4-2-[PtCl(9-ethylguanine)(NH$_3$)(isoquinoline)]$^+$.

31. A platinum coordination compound wherein said platinum coordination compound is a salt, the cationic component of which is trans-[PtCl(9-ethylguanine)(4-picoline)$_2$]$^+$.

32. A platinum coordination compound wherein said platinum coordination compound is a salt, the cationic component of which is SP-4-2-[PtCl(1-methylcytosine)(NH$_3$)(thiazole)]$^+$.

33. A platinum coordination compound wherein said platinum coordination compound is a salt, the cationic component of which is SP-4-2-[PtCl(1-methylcytosine)(NH$_3$)(quinoline)]$^+$.

34. A platinum coordination compound wherein said platinum coordination compound is a salt, the cationic component of which is SP-4-2-[PtCl(1-methylcytosine)(NH$_3$)(isoquinoline)]$^+$.

35. A platinum coordination compound wherein said platinum coordination compound is a salt, the cationic component of which is SP-4-2[PtCl(Me$_2$SO)(NH$_3$)(L')]$^+$, and wherein L' is a substituted or unsubstituted heterocyclic amine.

36. The compound of claim 35 wherein said substituted or unsubstituted heterocyclic amine is selected from the group consisting of thiazole, benzothiazole, isoquinoline, pyridine, and substituted pyridine.

37. A method for water-solubilizing a trans-platinum compound of the general formula trans-[PtX$_2$(L)(L')], where L and L' are NH$_3$ or a heterocyclic amine and X is an anionic ligand, and wherein L and L' cannot both be NH$_3$, comprising, replacing one X substituent with substituent selected from the group consisting of a sulfoxide, a heterocyclic nucleobase and hydantoin, wherein said step of replacing renders said trans-platinum compound water-soluble.

38. The method of claim 37 wherein said water-solubilization confers in vivo anti-tumor activity on said compound.

* * * * *